United States Patent [19]

Bernard

[11] Patent Number: 5,528,039
[45] Date of Patent: Jun. 18, 1996

[54] METHOD AND APPARATUS FOR LINEARIZATION OF NON-DISPERSIVE INFRARED DETECTOR RESPONSE

[75] Inventor: Bernie B. Bernard, College Station, Tex.

[73] Assignee: O.I. Corporation, College Station, Tex.

[21] Appl. No.: 396,563

[22] Filed: Mar. 1, 1995

[51] Int. Cl.$^6$ .................................................. G01N 21/61
[52] U.S. Cl. ............................................ 250/343; 250/344
[58] Field of Search ........................... 250/252.1 A, 343, 250/344; 356/437

[56] References Cited

U.S. PATENT DOCUMENTS

| | | | |
|---|---|---|---|
| 4,290,296 | 9/1981 | Bredeweg et al. | 73/1 G |
| 4,355,233 | 10/1982 | Warnke et al. | 250/343 |
| 4,581,714 | 4/1986 | Reid | 364/571 |
| 4,849,636 | 7/1989 | Fertig, Sr. | 250/252.1 A X |
| 5,297,419 | 3/1994 | Richardson | 73/25.03 |
| 5,357,113 | 10/1994 | Liston et al. | 250/344 |

FOREIGN PATENT DOCUMENTS 2341857  9/1977  France ................................. 250/344

*Primary Examiner*—Carolyn E. Fields
*Assistant Examiner*—Edward J. Glick
*Attorney, Agent, or Firm*—Arnold, White & Durkee

[57] ABSTRACT

A method and apparatus for adjusting the raw, instantaneous response of an NDIR and determining a linear response therefrom is disclosed. The NDIR detector cell is connected to an output which is adjusted according to the function $(Ax)/(1-x)$ where the coefficient A is a constant for the NDIR being used, and x is the raw, instantaneous, response of the detector. The coefficient A is determined by assessing the maximum response of the NDIR with an infinite mass of analyte within the sample cell.

5 Claims, 3 Drawing Sheets

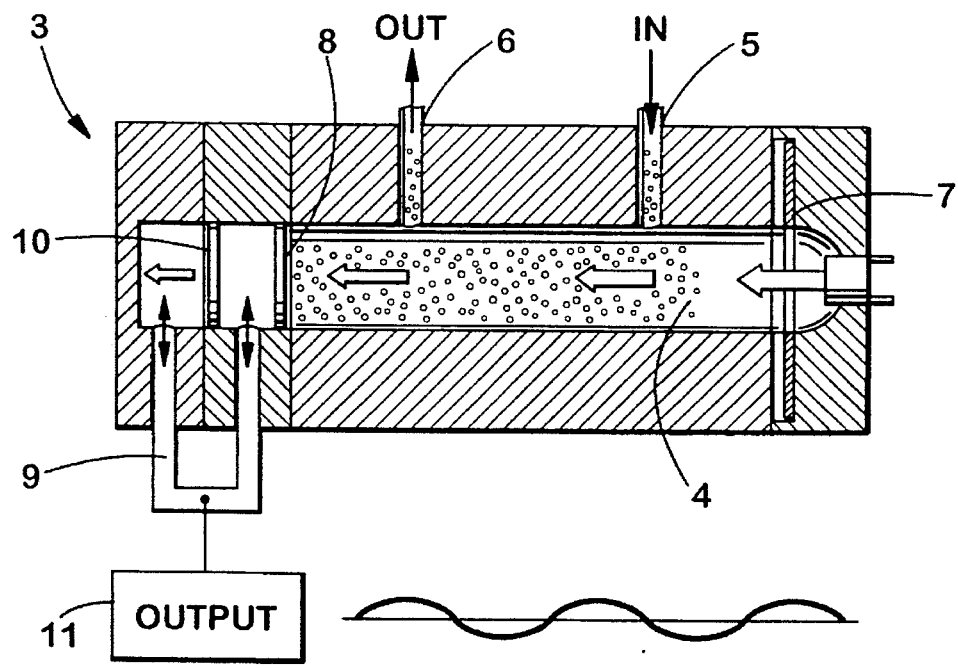
Fig. 3
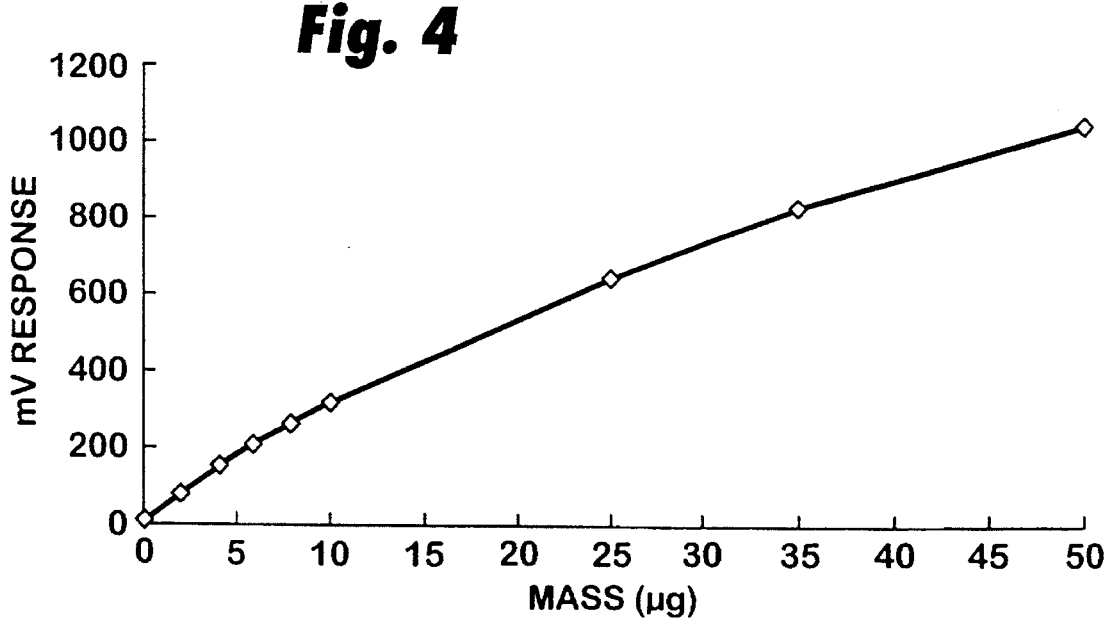

METHOD AND APPARATUS FOR LINEARIZATION OF NON-DISPERSIVE INFRARED DETECTOR RESPONSE

BACKGROUND OF THE INVENTION

1. Field of the Invention

This invention relates generally to non-dispersive infrared detectors for detecting small quantities of analyte gases. More specifically, the present invention relates to a method and apparatus for linearization of the response of a non-dispersive infrared detector in relation to the concentration or mass of the analyte gas.

2. Description of the Related Art

Infrared radiation detectors are used to monitor industrial process gas streams, in the medical field, for air pollution and respiratory measurements, and in laboratory applications.

Infrared radiation is an electromagnetic radiation. Any object whose temperature is above absolute zero radiates energy in relationship to the object's temperature. Infrared radiation detectors convert energy of infrared radiation into some other form of energy which may be processed more rapidly. In most cases, this conversion is from electromagnetic radiation energy into electrical energy. Infrared detectors may be classified as thermal detectors or photon detectors.

Thermal detectors are energy detectors, and their spectral response is dependent on the absorption properties of the detector. In such a detector, a thermal mass changes temperature as the impinging radiation changes. Several methods have been used to convert the temperature change of the mass into a usable electrical signal. These methods include the following: thermistor bolometer, thermopile detector, pyroelectric detector, and condenser microphone (Luft) detector. The majority of commercial infrared gas analyzers employ Luft detectors.

Photon detectors utilize the interactions of incident photons with the detector element. If the incident photon energy is sufficient to liberate an electron from the detector surface, then the so-called external photo-electric effect has occurred. When the incident photon merely liberates a free electron or a free hole or both in the body of the detector, then the internal photoelectric effect has occurred.

A fundamental difference between thermal detectors and photon detectors is that thermal detectors measure the rate at which energy is absorbed, while photon detectors measure the rate at which quanta are absorbed.

For many years, the absorption of radiation at certain wavelengths by gases has been used as a means of identifying and estimating them. When analyzing gasses, the vibrational spectra are of more practical interest than the rotational spectra. In general, infrared gas analysis methods may be either dispersive or non-dispersive. Dispersive methods are generally only suitable for laboratory use because of cost and fragility. Non-dispersive methods have been developed and are in widespread use.

Non-dispersive infrared detectors (NDIRs) consist of: (a) a suitable source of infrared radiation whose emission spectrum embraces the main absorption bands of the gases or vapors to be measured; (b) a measuring cell (or sample cell) through which the gas and radiation flow, containing the specimen of the gas or vapor stream to be analyzed, fitted with windows possessing suitable transmission properties; (c) means of restricting the wavelength range falling on the detector, such as an optical or gas filter; (d) means to modulate the infrared radiation from the source, such as a rotating chopper disk; (e) a detector block including a transducer in the form of an infrared detector to transform the infrared radiation into a corresponding electrical signal; (f) an amplifier for amplifying the detector signal; and (g) an output device.

Non-dispersive infrared detectors detect small quantities of gases that are non-symmetric in molecular structure in a matrix of diatomic or inert gas. Examples of non-symmetric gases that absorb energy in the infrared region include: carbon dioxide, carbon monoxide, nitrogen oxides, and sulfur dioxide. Examples of diatomic or inert gas matrices include: nitrogen, oxygen, helium, hydrogen, or a mixture of these (such as air). NDIRs can be made to be highly selective for one analyte over another, and are completely free of interference from a diatomic or inert gas matrix. This selectivity has made NDIRs the detectors of choice for certain analytical methods, including ambient air analysis for the above mentioned analytes and water analysis for total organic carbon.

Two drawbacks to using an NDIR in these and other analytical applications are: (1) relatively small dynamic range; and (2) inherent lack of linearity of the response. NDIRs typically can detect and reliably distinguish between about three orders of magnitude (i.e., a dynamic range of 1000), while other common detectors have dynamic ranges of five or six orders of magnitude. Part of the reason for this is because of a lack of linearity of the NDIR response.

As discussed above, the principle of operation of an NDIR is based on absorption of infrared energy by the analyte of interest due to the passage of the analyte through the measuring or sample cell, and the measurement of the subsequent decrease in light energy impinging the detector block.

One problem with NDIRs is that the response is not linear at higher points of analyte concentration, particularly at the upper end of the dynamic range of the NDIR. The relationships of the parameters and geometries involved cause the response to follow the Beer-Lambert Law to a large extent, but the response becomes attenuated at higher analyte concentrations. This aspect of the Beer-Lambert Law dictates an inverse logarithmic behavior of transmitted light energy as a function of the concentration of the analyte, so a linear response with increasing concentration is not anticipated. Due to various geometries of detectors, flows, and analytical methods, however, when the results of calibration runs are corrected according to the Beer-Lambert Law, linearity of the response is typically still not achieved.

In an attempt to provide a linear response, some NDIR designs have included analog electronic amplifiers which divide or segment the response into several steps at each level of analyte concentration within the dynamic range of the detector. For example, ten or eleven amplified steps may cover the entire range of the detector. These amplifiers are adjusted potentiometrically by trial and error in an attempt to cause the output of the NDIR at each level of analyte concentration to respond linearly with increasing concentration. The electronic amplification of NDIR responses has certain advantages, but the output is a non-continuous function because each segment is amplified separately.

At some point, increasing the portion of analyte gas in the flowing stream causes no further attenuation of light energy for a given NDIR system. This is because the analyte gas in the cell is already absorbing all of the radiation, and light transmittance at the detector cannot be reduced below zero.

In other words, the detector cannot measure any further decrease in light transmittance through the cell. Near these levels, the response of the NDIR is very low for a given concentration change, as compared to the response with lower concentrations. At these levels, if the response is segmented and amplified, as discussed above, the amplifier responsible for bringing this raw signal into linearity with lower sections of the response curve must amplify the signal as much as 500 to 1000 percent. In contrast, lower sections of the raw signal need to be amplified only 10 to 20 percent. As a result, small errors in the raw signal get amplified excessively, and accuracy is diminished. In practice, the operator must determine the working upper limit of analyte concentration that can be determined and distinguished from slightly different concentrations, based on this asymptotic behavior and the extent of this type of tolerance.

SUMMARY OF THE INVENTION

The present invention addresses these problems and disadvantages by providing a method and apparatus for adjusting the raw, instantaneous response of an NDIR and determining a linear response therefrom. The present invention includes an NDIR with a detector cell connected to output which is adjusted according to the function $(Ax)/(1-x)$ where the coefficient A is a constant for the NDIR being used, and x is the raw, instantaneous, response of the detector. Use of the function requires determining the coefficient A by assessing the maximum response of the NDIR with an infinite mass of analyte within the sample cell.

By adjusting the response at least every second, and preferably as often as every tenth of a second using the above function, the present invention provides a response that is linear and continuous over the calibrated range. Additionally, the present invention provides a higher maximum linear detection limit and extends the range of the NDIR over previously available methods and devices. The present invention also can provide single point calibration at any analyte concentration.

BRIEF DESCRIPTION OF THE DRAWINGS

FIG. 3 is a section view of an NDIR for use with the present invention, with the light source and with a sample flowing through the sample cell.

FIG. 4 is a graph of an NDIR response versus mass or concentration of the sample, before the response is adjusted according to the present invention.

DESCRIPTION OF A PREFERRED EMBODIMENT

Figure 1:
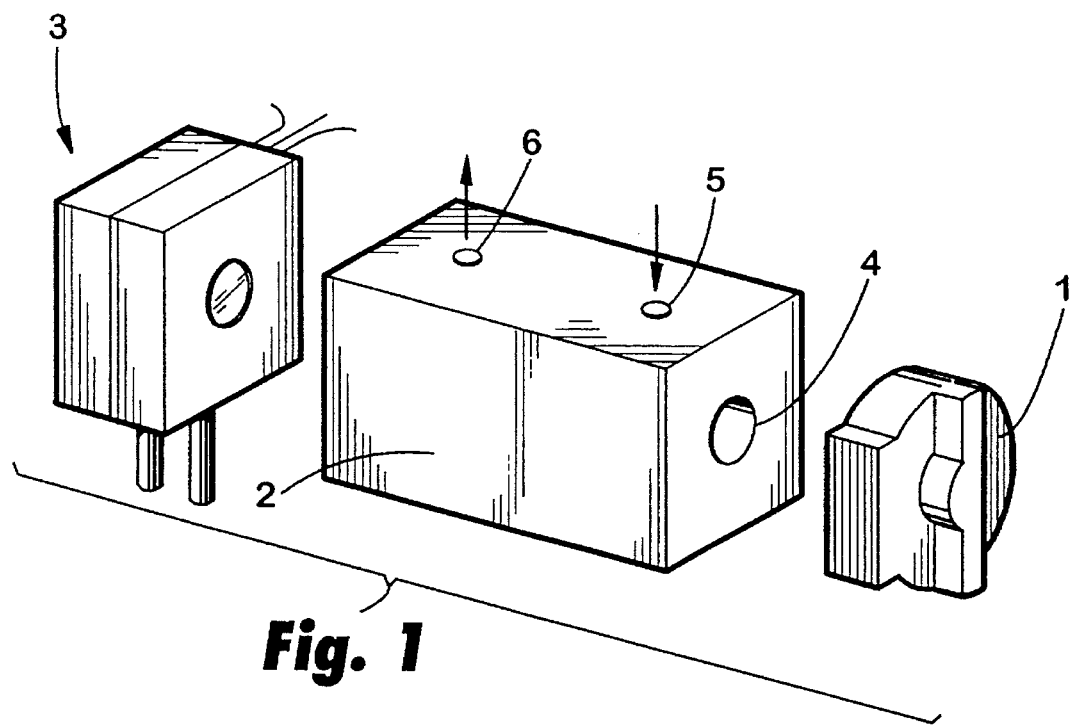
FIG. 1 is a perspective view of the light source, sample cell and detector cell for the NDIR used with the present invention.

FIG. 1 shows an infrared light source 1, sample cell 2 and detector cell 3 used with an NDIR according to the present invention. The sample enters passage 4 in the sample cell through sample inlet 5 and exits through sample outlet 6.

Figure 2:
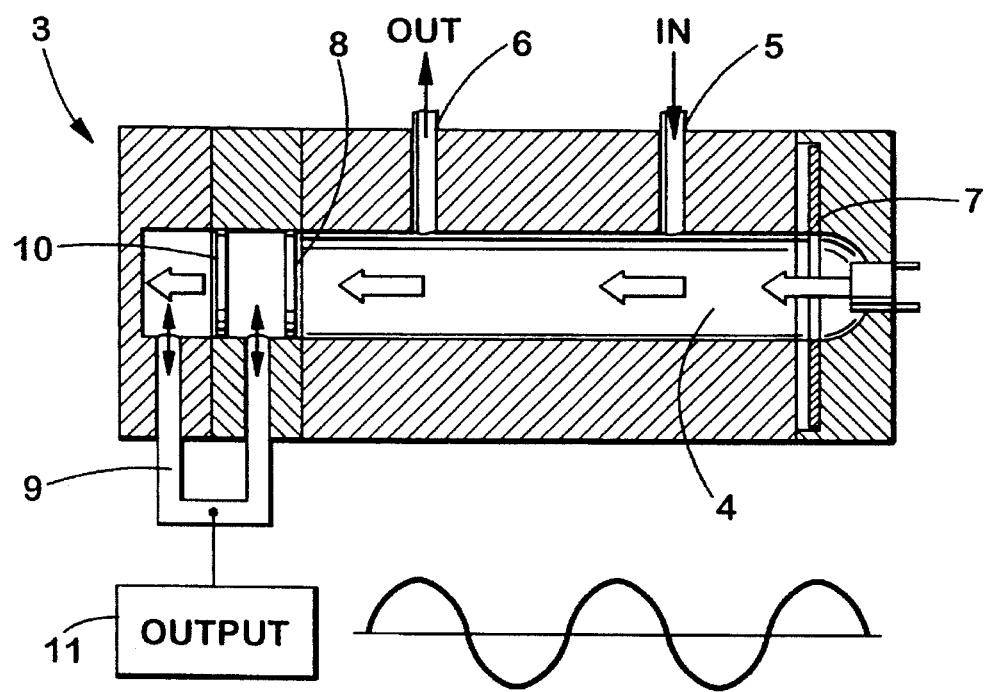
FIG. 2 is a section view of an NDIR for use with the present invention, with the light source on, and without a sample flowing through the sample cell.

As shown in FIG. 2, the NDIR also includes a chopper blade 7 to chop the infrared light into a series of pulses. The detector cell 3 includes a window 8 which is transparent to the infrared light, and a pathway 9 for reference gas which may flow to either side of a membrane or other barrier 10 connected to a pressure sensor. The pressure sensor produces output 11 depicted in FIG. 2 as a sine wave, representing the amount of light reaching the detector. Depending on the reference gas, the output is indicative of the compounds present in the sample gas.

As shown in FIG. 3, when a sample gas is present in the passage 4 of the sample cell, the amount of infrared energy reaching the detector is diminished. The output 11 from the pressure sensor is likewise lower, depicted as the sine wave shown in FIG. 3, representing a reduced amount of light reaching the detector.

In FIG. 4, the raw, instantaneous, response of the NDIR is plotted against the mass or concentration of the sample. The response is shown in mV while the mass is in milligrams. As the sample mass or concentration increases, the response tends to plateau such that greater concentrations of the sample gas fail to provide adequate response, indicating a limited range of the detector.

According to the present invention, the raw, instantaneous, detector response x is operated on with the following function, to provide a linearized response y:

$$y=(Ax)/(1-x)$$

Figure 5:
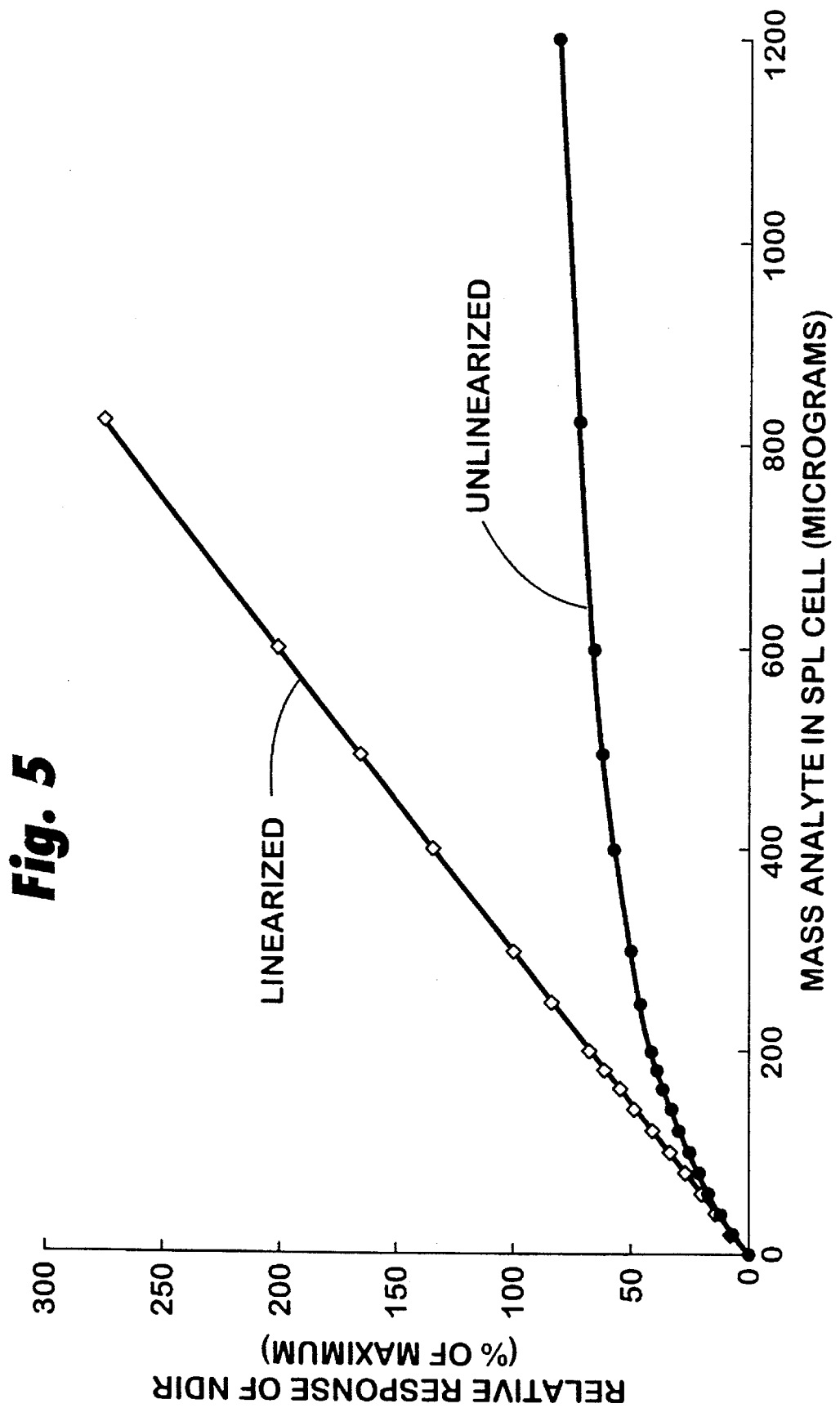
FIG. 5 is a graph of an NDIR response versus mass or concentration of the sample, after the response is adjusted according to the method and apparatus of the present invention.

The coefficient A is the maximum response of the detector with infinite mass of analyte (the asymptote of the response curve). As discussed previously, and as shown in FIG. 5, at some point the response curve plateaus while sample mass or concentration is still being increased. The coefficient A is the detector response at the point where the response curve flattens out. The coefficient A is fixed for a given detector, and can be determined by essentially blocking the light path with 100% concentration of sample.

Once the coefficient A is known, a computer or microprocessor is used to provide the linearized response from the raw, instantaneous, sample response at regular intervals. This should be done at least every second, and preferably every tenth of a second.

Although variations in the embodiment of the present invention may not each realize all the advantages of the invention, certain features may become more important than others in various applications of the device. The invention, accordingly, should be understood to be limited only by the scope of the appended claims.

What is claimed:

1. A nondispersive infrared gas analyzer comprising:
   (a) an infrared light source;
   (b) a detector cell;
   (c) a sample cell having a passage therein for a sample gas to be analyzed, the sample gas including an analyte which is a component of the sample gas, the passage extending between the infrared light source and the detector cell;
   (d) output means operatively connected to the detector cell for providing instantaneous response x indicative of the sample gas; and
   (e) means for providing a linearized response at regular intervals at least as often as every second, using the function $(Ax)/(1-x)$, where A is the maximum response of the detector cell with infinite mass of the analyte.

2. The nondispersive infrared gas analyzer of claim 1 further comprising means for modulating the infrared light source.

3. The nondispersive infrared gas analyzer of claim 1 further comprising means for restricting the wavelength range of the infrared light source reaching the detector cell.

4. The nondispersive infrared gas analyzer of claim 1 wherein the detector cell includes means for transforming the infrared radiation into an electrical signal.

5. A method for providing a linearized response from a raw, instantaneous, response x from an NDIR gas analyzer having an infrared light source, detector cell and sample cell, the response inversely related to the amount of infrared light passing through the sample cell that reaches the detector cell, comprising the steps of:

(a) determining the maximum response A when infrared light is blocked from reaching the detector cell;

(b) sampling the raw, instantaneous response of the detector cell at least as often as every second; and (c) applying the function $(Ax)/(1-x)$ to each sample of the raw instantaneous response X.

* * * * *